United States Patent [19]

Pugia

[11] Patent Number: 5,753,455
[45] Date of Patent: May 19, 1998

[54] METHOD FOR THE DETECTION OF LYSOZYME USING A PROTEIN ERROR INDICATOR DYE IN CONJUNCTION WITH AN ALKANE SULFONIC ACID

[75] Inventor: Michael J. Pugia, Granger, Ind.

[73] Assignee: Bayer Corporation, Pittsburgh, Pa.

[21] Appl. No.: 709,229

[22] Filed: Sep. 3, 1996

[51] Int. Cl.[6] .................. C12Q 1/34; C12Q 1/28
[52] U.S. Cl. .................. 435/18; 435/28; 436/904
[58] Field of Search .................. 435/18, 25, 28; 422/56, 57; 436/86, 88, 169, 904

[56] References Cited

U.S. PATENT DOCUMENTS

| | | | |
|---|---|---|---|
| 5,087,575 | 2/1992 | Lau | 436/166 |
| 5,279,790 | 1/1994 | Corey et al. | 422/55 |
| 5,424,215 | 6/1995 | Albarella et al. | 436/86 |
| 5,593,895 | 1/1997 | Cahill et al. | 436/86 |

OTHER PUBLICATIONS

Kragh–Hansen U., Relation Between Binding of Phenolsulfophthalein Dyes and Other Ligands With a High Affinity for Human Serum Albumin. Biochimica et Biophysica Acta 365:360–371, 1974.

Y. Fujita, Bunseki Kagaku, vol. 32, pp. E379–E386, 1983 "Color Reaction Between Pyrogallol Red—Molybdenum (VI) Complex and Protein".

Kragh–Hansen et al., Biophysics Acta, (365), pp. 360–371 (1974) Protein Binding of Small Molecules.

Macart et al., Clinica Chimica Acta, (141), pp. 77–84 (1984) Evaluation of an Improved Coomassie Dye Binding Method for Urinary Protein Assay.

*Primary Examiner*—Ralph Gitomer
*Attorney, Agent, or Firm*—Jerome L. Jeffers

[57] ABSTRACT

The determination of lysozyme in urine is carried out by contacting the urine with a reagent system containing a buffer and a protein error indicator dye. Other proteins normally found in urine can compete with the lysozyme for interaction with the protein error indicator thereby affecting the specificity of the test for lysozyme. The present invention involves the addition of certain alkyl sulfonic acids or sulfonates to increase both specificity and sensitivity of the reagent for lysozyme.

10 Claims, No Drawings

METHOD FOR THE DETECTION OF LYSOZYME USING A PROTEIN ERROR INDICATOR DYE IN CONJUNCTION WITH AN ALKANE SULFONIC ACID

BACKGROUND OF THE INVENTION

The present invention relates to the detection of lysozyme in aqueous fluids, e.g. urine, by the use of a test system containing a protein error indicator and a buffer. The determination of the presence of protein in a urine sample is important because lysozymuria is a useful indicator of damage to the tubular cells of the kidney and as a diagnostic aid in monocytic myelomonocytic leukemia. In addition, lysozymuria may indicate pyelonephritis, homograft rejection or heavy metal poisoning. Thus, it is often necessary to qualitatively and quantitatively measure lysozyme in urine.

Various methods for determining the presence of protein in urine are known, the most convenient of which involves wetting an absorbent strip impregnated with a protein error indicator and a buffer with a small quantity of urine. Protein error indicators are pH indicators which contain an ionizable group which is displaced in the presence of protein to provide a detectable color change. This is the same color change that the indicator would undergo under the influence of a pH change, so it is important to include a buffer in the test system to thereby avoid a pH increase since such an increase could cause a color change in the indicator in the absence of protein thereby resulting in a false positive result.

Protein detection methods based on the binding of protein error indicators such as phenolsulfonephthalein dyes are relatively nonspecific means of protein determination. The present invention involves the use of alkyl sulfonic acids and/or their salts to increase the sensitivity of methods based on the binding of protein error indicators such that lysozyme can be accurately detected.

U.S. Pat. No. 5,187,104 discusses the use of 5',5"-dinitro-3',3"-diiodo-3,4,5,6-tetrabromophenolsulfonephthalein (DIDNTB) dye in a protein detection method and mentions the use of color enhancing polymers in a combination with the reagents. Specific polymers mentioned are polypropylene glycols, poly(propylene ether carbonate) and polyvinylethers. Also mentioned is the polyether carbonate designated as KOK 10.002 from Bayer AG, a propylene oxide and ethylene oxide adduct of 1,6-dimethyl-4-nonylphenol available from Bayer AG under the tradename Fenoil D4030 and a polyvinyl ether available under the designation Lutonal ISO from BASF.

In U.S. Pat. 5,124,266 there is described the use of a test strip for protein in urine in which a bibulous carrier matrix containing a protein error indicator and a buffer is treated with a polymerized urethane based compound to resist the formation of background color to thereby improve the sensitivity of the test strip.

The use of polyvinyl alcohol has been described in conjunction with protein tests based on metal chelating dyes by Y. Fujiti in Bunseki Kagaku (32) 379–386 (1983). This reference describes polyvinyl alcohol and polyvinyl pyrolidone as suitable nonionic surfactants for unicel formation but does not mention any increase in the specificity for particular proteins.

Several studies have been carried out on the effects of long chain alkyl groups on the binding of protein error indicators to proteins. The effects of long chain alkyl carboxylic acids, such as palmitic acid, on the binding of protein error indicators has been described by Kragh-Hansen et al. in Biophysics Acta, (365), 360–371 (1974). Palmitate was shown to have modest inhibitory effects on the binding of phenyl red to albumin; other proteins were not studied. Based on this, one would not expect alkyl groups, long chain or otherwise, to alter specificity.

Other studies have shown that long chain alkyl sulfonic acids, such as sodium dodecyl sulphate, affect the binding of protein error indicators. Work described by Macart et al. in Clinica Chimica Acta (144), 7–84 (1984) and Perini et al. in Clinica Chimica Acta (143), 321–323 (1984) showed that sodium dodecyl sulfonate equalized the differences in the sensitivity of Coomassie Brilliant Blue (CBB) to various proteins and decreased the specificity of the test for albumin but did not increase the sensitivity for any other protein.

SUMMARY OF THE INVENTION

The present invention involves the semi-quantitative analysis of lysozyme in an aqueous test sample which analysis is carried out by contacting the fluid suspected of containing lysozyme with a test reagent comprising a protein error indicator dye which undergoes a detectable color change when contacted with protein in a buffered solution. There is presently disclosed a method which comprises adding to the test reagent an alkyl sulfonic acid having from 9 to 15 carbon atoms or a salt of said sulfonic acid wherein the size of the alkyl group and the concentration of alkyl sulfonic acid in the aqueous test sample are such that the detectable color change is caused by lysozyme in the test sample but a detectable color change is not caused by human serum albumin and/or IgG or other urinary protein present in the sample.

DESCRIPTION OF THE INVENTION

In accordance with the present invention, it has been discovered that certain alkyl sulfonic acids and/or salts thereof increase the response of a protein error indicator to lysozyme and reduce the response to human serum albumin, IgG and other urinary proteins. Since human serum albumin is typically present in urine (albeit normally in small amounts) the use of the alkyl sulfonic acids of the present invention provides a method for the detection of lysozyme in the presence of other urinary proteins. Those selective inhibitors that may inhibit the protein error indicator response to human serum albumin and/or IgG while increasing the response to lysozyme are desirable additives to a reagent for determining the concentration of lysozyme because of the resulting increase in specificity for lysozyme which such a system provides. The effect of the materials of the present invention is not just inhibition; they also increase (activate) the lysozyme response. Those materials which are useful in the present invention are the straight or branched chain alkyl sulfonic acids of 9 to 15 carbon atoms with chain lengths of 10 to 12 carbon atoms being preferred. Also suitable for use in the present invention are salts of the alkyl sulfonic acids. In this regard, suitable cations include, but are not limited to, sodium, potassium, lithium, magnesium or calcium.

One aspect of the present invention is directed to an analytical test strip for the detection of lysozyme in urine which comprises an absorbant carrier impregnated with a suitable protein error indicator, a suitable buffer and the alkyl sulfonic acid or sulfonate. Suitable protein error indicators include Tetrabromophenol Blue (TBPB), the aforementioned DIDNTB, Coomassie Brilliant Blue, Fast Green FCF, Light Green SF, pyrogallol red and pyrocatechol violet. In addition, the merocyanine and nitro or nitroso substituted polyhalogenated phenolsulfonephthaleins disclosed in U.S. Pat. No. 5,279,790 may be used.

The absorbant carrier of the test strip is preferably filter paper. Other materials useful as the absorbant carrier include felt, porous ceramic strips and woven or matted glass fibers such as those described in U.S. Pat. No. 3,846,247. Also suitable are wood, cloth, sponge material and argillaceous substances such as those described in U.S. Pat. No. 3,552,928. Alternatively, the absorbant carrier can be of a nonporous material such as a polymeric film or glass.

In preparation of the strip, the absorbant carrier is impregnated with a solution of the protein error indicator, buffer and the selective inhibitor. This impregnation is normally carried out by a two dip procedure in which the first dip comprises water or a water/polar organic solvent mixture in which there is dissolved a buffer. After drying, the strip is dipped into a second solution of an organic solvent in which is dissolved the protein error indicator which is typically present at a concentration of from about 0.2 to 5.0 mM and the sulfonic acid or sulfonate inhibitor.

After dipping and drying, the strips are ready for use which normally involves dipping them into a urine sample and reading the response resulting from the color change in the indicator which reading is conducted either manually or by use of a reflectance spectrometer for better quantitation.

The pH at which the assay is conducted will depend on the particular protein error indicator dye which is used in the reagent formulation. The buffers which are most compatible with a particular dye are known or can be readily determined through routine experimentation.

The method of practicing the present invention is further illustrated by the following examples. These examples and the data contained therein demonstrate the desirability of using alkyl sulfonic acids or sulfonates, as described above, to increase the sensitivity of the dye binding method for lysozyme thereby enhancing the value of urinary lysozyme determinations. The present invention provides a method for the determination of lysozyme without interference by other urinary proteins.

EXAMPLE I

The DIDNTB protein reagent was made from two saturations of Alhstrom 204 filter paper. The first saturation was with an aqueous ethanol mix containing tartaric acid as buffer and methyl red as background dye. The mix pH was adjusted to 2.1 using sodium hydroxide and/or hydrochloric acid. The second saturation was a toluene/THF mix containing the protein indicator dye, DIDNTB, and Lutanol M40 [poly(vinyl ether)] as enhancer polymer. The function, concentration and allowable ranges of each ingredient are set out in Table 1. The alkyl sulfonic acid and sulfonates can be added to either the aqueous or organic solvent mix depending on solubility.

TABLE 1

DIDNTB Protein Reagent Composition

| Ingredient | Function | Conc. Used | Allowable Range |
|---|---|---|---|
| 1st application | | | |
| Water | Solvent | 1000 mL | — |
| Methyl red | Background dye | 9.5 mg | 0–10 mg |
| Ethanol | Solvent | 100 g | 0–40 g % |
| Tartaric acid | Buffer | 64 g (280 mM) | 50–750 mM |
| Alkyl sulfonic acid/sulfonate | | See Table 2 | 0.01 to 4 g % |
| pH | — | 2.1 | 1.5–3.5 |
| 2nd application | | | |
| Toluene | Solvent | 95 mL | — |
| THF | Solvent | 5 mL | 0–50 mL |
| DIDNTB | Indicator | 65.7 mg (0.6 mM) | 0.2–5.0 mM |
| Lutonal M40 | Polymer enhancer | 0.143 g % | 0–1.0 g % |
| Alkyl sulfonic acid/sulfonate | | See Table 2 | 0.01 to 4 g % |

DIDNTB = 5',5", Dinitro-3',3"-Diiodo-3,4,5,6-Tetrabromophenolsulfonephthallein

At the lower end of the concentration range, most alkyl sulfonic acids/sulfonates would be expected to be water soluble. At higher concentrations in the case of more complex alkyl groups, organic solvents are preferred. The mix solutions were used to saturate the filter paper which was dried for 7 minutes after each saturation. The resultant dry reagents were processed into reagent strips which were tested on a CLINITEK-200+™ instrument after being dipped in urine containing either 0 or 30 mg/dL human serum albumin (HSA) or an 80 mg/dL mixture of other urinary proteins such as Tamm Horstall, alpha-1-microglobulin, glycoprotein, transferrin or alpha-1-glycoprotein, as well as 300 mg/dL each of lysozyme and IgG.

The HSA containing urine sample was first filtered through an ultrafiltration membrane with a 10 KDa molecular weight cut-off to remove naturally occurring HSA prior to the addition of the 30 mg/dL of HSA.

The total protein containing urine sample was collected by using an immunological HSA assay and the Coomassie Brilliant Blue CBB method to screen over 175 clinical samples providing a comprehensive ALBUSTIX™ result. Four specimens out of the 175 were identified as having less than 1.2 mg/DL albumin, IgG and lysozyme by immunological assays. The urines were pooled and diluted to 40 or 80 mg/dL protein. The reagent response was measured on a CLINITEK-200+™ as the result of 1000×Reflectance @610 nm/% Reflectance @690 nm. The difference between negative and protein containing urines was taken as the protein response. The response of control formula lacking alkane sulfonate was compared to the composition containing alkane sulfonate to determine the % change in response. The data from this experiment are tabulated in Table 2:

TABLE 2

Comparison Carboxylic and Sulfonic Acids

| Additive | Protein Response in CLINITEK-200 decodes Expressed as difference between Negative and | | | |
|---|---|---|---|---|
| | 300 mg/dL Lysozyme | 30 mg/dL HSA | 300 mg/dL IgG | 80 mg/DL Urinary Protein |
| None | 313 | 704 | 462 | 650 |
| Decanol | 243 | 674 | 532 | 700 |
| Decane carboxylic acid | 113 | 677 | 507 | 649 |
| Hexadecane Carboxylic acid | 98 | 637 | 464 | 636 |
| Hexanesulfonic acid 6 mM | 274 | 758 | 556 | 854 |
| Octanesulfonic acid 6 mM | 401 | 632 | 536 | 715 |
| Decanesulfonic acid 6 mM | 885 | 337 | 428 | 334 |
| Dodecane sulfonate 6 mM | 803 | 74 | 232 | 228 |
| Hexadecane sulfonic acid 6 mM | 368 | 757 | 498 | 705 |
| Poly (vinylsulfonic acid) 0.2% | 322 | 321 | 406 | 341 |

From Table 1 it can be determined that sulfonic acids with an alkyl group comprising decane or dodecane are effective to enhance the lysozyme response while also inhibiting the response of HSA and the other urinary proteins. From these data, one can fairly extrapolate that straight or branched chain alkyl sulfonic acids in which the alkyl group is $C_9$ to $C_{15}$ would be effective in enhancing the lysozyme response while inhibiting that of HSA and the other proteins. Sulfonic acid or a sulfonate with a $C_{12}$ alkyl group would be preferred. The response of the reagent to 15 mg/dL was 532 decodes. In the case of IgG, a reduced response was observed at 300 mg/dL. No detectable response was observed at 50 mg/dL IgG or 40 mg/dL urinary protein. In addition to alkane sulfonic acid, $C_9$ to $C_{15}$ alkane sulfonate salts in which the cation is, for example; Na, K, Li, Mg or Ca are suitable for use in the present invention. In contrast, alkyl carboxylic acids such as hexadecane carboxylic acid and decane carboxylic acid inhibited the lysozyme but did not inhibit the response of HSA or the other urinary proteins. The polymeric additive, poly(vinylsulfonic acid) was found not to affect lysozyme while inhibiting the HSA response.

EXAMPLE II

The concentration of sodium dodecane sulfonate needed for effectiveness was tested as described above with the results being set out in Table 3. The effect was noted at concentrations greater than 0.8 mM or 25% of the concentration of the DIDNTB indicator. The effect was not reduced by excess sodium dodecane sulfonate which had the greatest benefit at 200% of the concentration of the DIDNTB indicator.

TABLE 3

The Effect of the Concentration of Sodium Dodecane Sulfonate

| Dodecane sulfonate | g % | Protein Response in CLINITEK-200 decodes Expressed as difference between Negative and | | |
|---|---|---|---|---|
| | | 300 mg/dL Lysozyme | 30 mg/dL Albumin | 150 mg/dL IgG |
| 6.0 mM | 0.2 | 803 | 74 | 232 |
| 1.5 mM | 0.05 | 821 | 305 | 326 |
| 0.8 mM | 0.026 | 643 | 492 | 299 |
| 0.2 mM | 0.001 | 369 | 706 | 367 |
| 0.0 mM | 0.0 | 331 | 704 | 462 |

EXAMPLE III

The effect of sodium dodecane was compared with another surfactant, Surfonyl® polyethylene oxide from Air Products Corporation. As can be determined from the data presented in Table 4, Surfonyl could be added to the reagent system as a typical surfactant but no improvement in the detection of lysozyme was noted.

TABLE 4

The Effect of the Concentration of Sodium Dodecane Sulfonate

| Dodecane sulfonate | Visual Response for 20 mg/dl | |
|---|---|---|
| | Lysozyme | HSA |
| Control | 20 | 49 |
| 0.2% Surfonyl | 18 | 50 |
| 0.5% Surfonyl | 15 | 48 |
| 1.0% Surfonyl | 14 | 50 |
| 0.05 mM dodecane sulfonate | 28 | 50 |
| 0.10 mM dodecane sulfonate | 28 | 46 |
| 2.00 mM dodecane sulfonate | 30 | 10 |

*Visual response measured by comparison to color chart. The higher the number the more color produced.

The surface tension of solutions containing sodium dodecane sulfonate or Surfonyl were compared, which comparison showed that although the 0.5% Surfonyl solution's surface tension was identical to that of the 2.0 mM dodecane sulfonate containing solution, there was no inhibition of the albumin response, thereby demonstrating the effect on lysozyme determination exhibited by sodium dodecy sulfonate is not due solely to its surfactant nature.

I claim:

1. In the semi-quantitative analysis of an aqueous test sample for lysozyme which test sample is suspected of containing lysozyme as well as human serum albumin and other proteins and which analysis is carried out by contacting the aqueous test sample suspected of containing the proteins with a test reagent comprising a protein error indicator dye and buffer which dye undergoes a detectable color change when contacted with the proteins, the improvement which comprises including in the test reagent straight or branched chain alkyl sulfonic acid wherein the alkyl group contains from 9 to 15 carbon atoms or a salt of said sulfonic acid, which alkyl sulfonic acid or sulfonate enhances the detectable color change caused by lysozyme present in the test sample thereby increasing the sensitivity of the analysis.

2. The analysis of claim 1 wherein the aqueous test sample is urine.

3. The analysis of claim 1 wherein the alkyl group is n-dodecyl.

4. The analysis of claim 1 wherein the salt of the alkyl sulfonic acid is the sodium, potassium, lithium, magnesium or calcium salt.

5. The analysis of claim 1 wherein the protein error indicator dye is a merocyanine or nitro-nitroso substituted polyhalogenated phenolsulfonephthalein.

6. The analysis of claim 1 wherein the protein error indicator dye is Tetra bromophenol Blue DIDNTB, Coomassie Brilliant Blue, Fast Green FCF, Light Green SF, pyrogallol red or pyrocatechol violet.

7. An analytical test strip for the detection of lysozyme in an aqueous test sample which strip comprises an absorbant carrier impregnated with a protein error indicator, a buffer and a straight or branched chain alkyl sulfonic acid containing from 9 to 15 carbon atoms or a salt thereof.

8. The test strip of claim 7 wherein the alkyl group of the alkane sulfonic acid or sulfonate is n-dodecyl.

9. The test strip of claim 7 wherein the absorbant material is filter paper.

10. The test strip of claim 7 wherein the protein error indicator dye is Tetrabromophenol Blue, DIDNTB, Coomassie Brilliant Blue, Fast Green FCF, Light Green SF, pyrogallol red or pyrocatechol violet.

* * * * *